United States Patent
Nocca

(10) Patent No.: US 10,898,361 B2
(45) Date of Patent: Jan. 26, 2021

(54) OROGASTRIC CATHETER FOR LONGITUDINAL GASTRECTOMY

(75) Inventor: David Nocca, Montpellier (FR)

(73) Assignee: Medical Innovation Developpement, Dardilly (FR)

(*) Notice: Subject to any disclaimer, the term of this patent is extended or adjusted under 35 U.S.C. 154(b) by 1142 days.

(21) Appl. No.: 13/805,916

(22) PCT Filed: Jun. 22, 2011

(86) PCT No.: PCT/EP2011/060428
§ 371 (c)(1),
(2), (4) Date: Feb. 20, 2013

(87) PCT Pub. No.: WO2011/161148
PCT Pub. Date: Dec. 29, 2011

(65) Prior Publication Data
US 2013/0165774 A1    Jun. 27, 2013

(30) Foreign Application Priority Data

Jun. 23, 2010   (FR) .................................... 10 54996

(51) Int. Cl.
*A61F 5/00*       (2006.01)
*A61M 25/10*     (2013.01)
(Continued)

(52) U.S. Cl.
CPC .......... *A61F 5/0089* (2013.01); *A61F 5/0083* (2013.01); *A61M 25/1002* (2013.01);
(Continued)

(58) Field of Classification Search
CPC ....... A61B 5/06; A61B 19/52; A61B 19/5244; A61B 19/5251; A61B 19/5272
(Continued)

(56) References Cited

U.S. PATENT DOCUMENTS 5,255,678 A * 10/1993 Deslauriers ............ A61B 5/042
600/375
5,401,241 A    3/1995 Delany
(Continued)

FOREIGN PATENT DOCUMENTS

WO    02/096327 A2    12/2002

*Primary Examiner* — Peter Luong
(74) *Attorney, Agent, or Firm* — Pearne & Gordon LLP

(57) ABSTRACT

The invention relates to an orogastric catheter for a longitudinal gastrectomy. The object of the invention is to make available an orogastric catheter that represents an advantageous alternative to the poorly suited catheters used today and that facilitates the work of the surgeon. This novel orogastric catheter is characterized in that this distal part carries a balloon (25) which, in the inflated state, has a shape substantially matching that of the pyloric antrum (4), in such a way as to be able to be lodged in this pyloric antrum (4), the end of the inflated balloon (25) then being in abutment against the pylorus (5), and the distal end of the body of the catheter (20) for its part being in abutment against the pyloric antrum (4), while the part of the body (21) of the catheter (20) arranged above the inflated balloon (25) is wedged against the wall of the lesser curvature (6) of the stomach (1), thus making it possible to determine the position of the start of the closure resection line in the area of the pyloric antrum (4), to define the closure resection line, and to calibrate the pyloric antrum (4) and the gastric sleeve to be preserved.

8 Claims, 6 Drawing Sheets

(51) Int. Cl.
*A61J 15/00* (2006.01)
*A61M 25/04* (2006.01)
*A61M 25/00* (2006.01)

(52) U.S. Cl.
CPC ........ *A61J 15/0003* (2013.01); *A61J 15/0049* (2013.01); *A61M 25/04* (2013.01); *A61M 2025/0008* (2013.01)

(58) Field of Classification Search
USPC ........................................................ 600/424
See application file for complete search history.

(56) References Cited

U.S. PATENT DOCUMENTS

| | | | | |
|---|---|---|---|---|
| 5,411,027 | A * | 5/1995 | Wiklund | A61B 5/06 600/18 |
| 5,735,290 | A * | 4/1998 | Sterman | A61B 17/00234 128/898 |
| 6,120,442 | A * | 9/2000 | Hickey | A61B 5/0215 600/300 |
| 2003/0065359 | A1 | 4/2003 | Weller et al. | |
| 2005/0251158 | A1 | 11/2005 | Saadat et al. | |
| 2006/0095066 | A1 * | 5/2006 | Chang | A61F 11/002 606/199 |
| 2006/0106361 | A1 * | 5/2006 | Muni | A61B 5/06 604/500 |
| 2006/0142787 | A1 | 6/2006 | Weller et al. | |
| 2010/0094116 | A1 * | 4/2010 | Silverstein | A61B 5/06 600/409 |

* cited by examiner

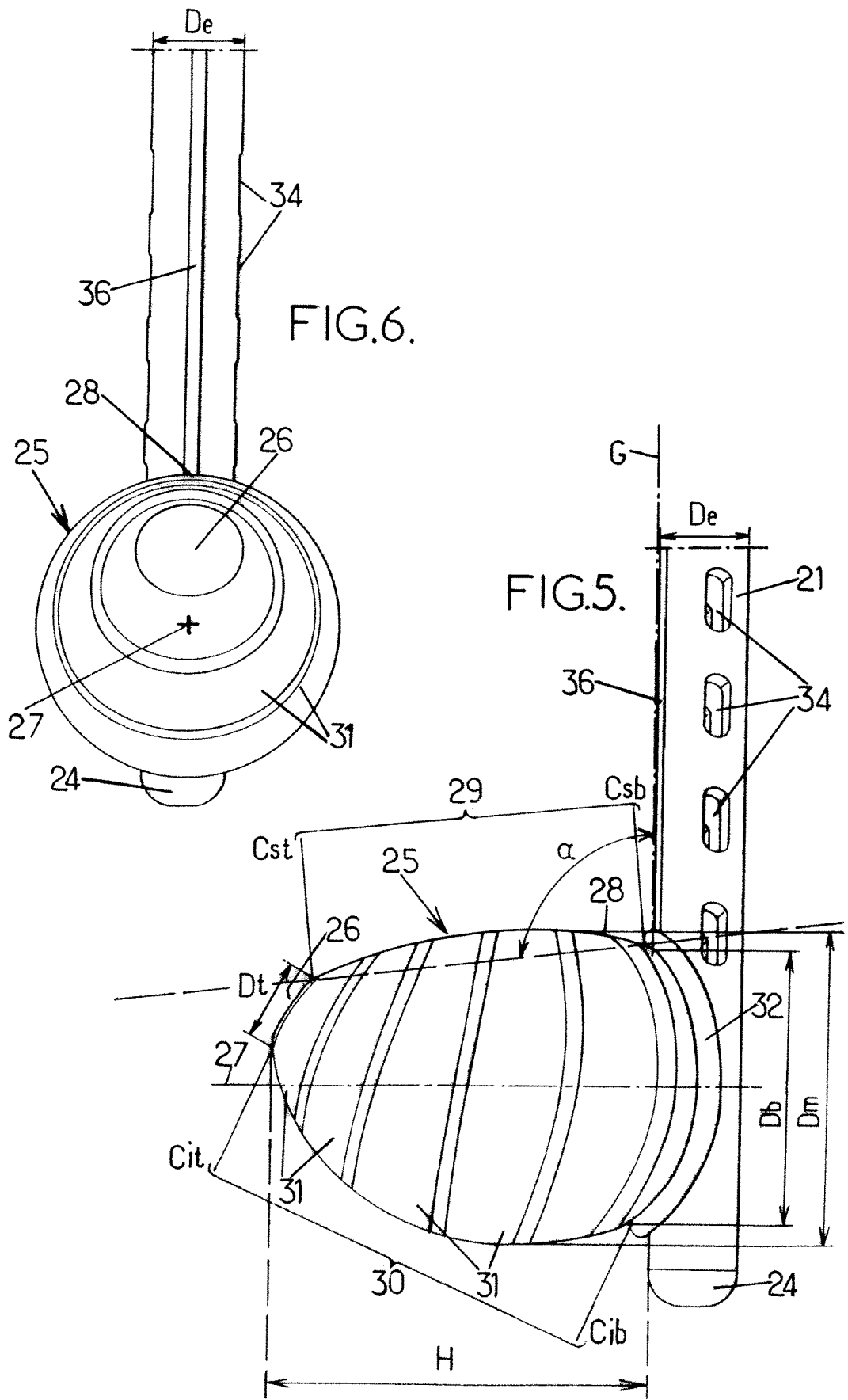

OROGASTRIC CATHETER FOR LONGITUDINAL GASTRECTOMY

FIELD OF THE INVENTION

The field of the invention is that of surgical instruments useful for surgeons performing techniques of gastric surgery. The instruments more particularly concerned are orogastric catheters for aiding the surgeon in the context of the bariatric surgical technique of longitudinal gastrectomy or sleeve gastrectomy.

TECHNOLOGICAL BACKGROUND

Orogastric catheters are in the form of transparent flexible tubes, for example made of silicone, open at both ends, proximal and distal. The distal part of these catheters has a whole series of lateral orifices allowing the passage of liquid and gaseous flows in both directions. Conventionally, gastric catheters have marks provided over their entire length allowing precise evaluation of the position in vivo.

These catheters may be intended for draining the stomach contents (air, secretions), for feeding the patient, for clarifying a diagnosis, for carrying out lavage, or, during an operation of bariatric surgery with longitudinal gastrectomy, for draining the stomach contents and to aid the surgeon in performing the longitudinal gastrectomy.

This surgical operation aims to reduce the capacity of the stomach (resection of about two thirds of the stomach) to produce a sensation of early satiety and to have an effect on weight loss.

During this operation, performed under general anaesthesia and in the vast majority of cases by coelioscopy, one or more gastric catheters are introduced via the patient's mouth and are lowered via the oesophagus to the level of the gastric antrum. The advantage of using these various catheters is, in the chronological order of the operation:

1) exsufflation of the stomach in the case of air distension caused by intubation manoeuvres during anaesthesia.
2) calibrating the gastric sleeve that remains by means of the tubular body of the catheter.
3) providing the surgeon with anatomic reference points for performing a high-quality resection while avoiding stenosis of the remaining part of the gastric tube (the surgeon resting against the body of the catheter to carry out the stapling).
4) injecting and then withdrawing liquid (methylene blue) in the patient's stomach, after stapling, to verify the hermeticity of the staple-line.

It should be noted that there are principally two methods of carrying out the so-called "sleeve gastrectomy" operation. These two methods are described below, referring to the accompanying FIG. 1, which shows a diagram of the stomach.

The first method, called "with conservation of the gastric antrum", consists of performing on the patient's stomach 1, by stapling, a staple-line -$LA_1$- in a straight line, from the angle of His -2- to a point -3- of the gastric antrum -4- at a distance ($a_1$) of 6 to 8 cm from the pylorus -5-.

The second method, called "without conservation of the gastric antrum", consists of making a staple-line -$LA_2$- at first concentric with the lesser curvature 6 of the stomach 1, from the angle of His -2- to the angulus or small tuberosity (cf. point of abutment of the distal end of the catheter in FIG. 1) -7- of the stomach -1-, then oblique to a point 8 located 2 cm ($a_2$) from the pylorus -5- (indicated by a dotted line in FIG. 1).

The use of a gastric catheter of the "Salem catheter" type for the withdrawal of air present in the patient's stomach (step 1), a catheter of the "Faucher tube" type for calibrating the gastric sleeve before the operation of closure resection (stapling-suture) (steps 2 & 3), and finally a catheter of the "Salem catheter" type for injection and withdrawal of gastric fluid at the end of the procedure (step 4), is known. This last-mentioned catheter can be left in place for some days, depending on the surgical teams' usual procedures.

This "Faucher tube" is shown in FIG. 2. It consists of a silicone tube 114 open at both ends and the wall has of which oblong openings 115 in its distal part. This catheter is provided with graduated positioning marks 10.

This Faucher tube is introduced into the stomach until its distal end is in abutment against the greater curvature -7- of the stomach. The body of the Faucher tube rests on the lesser curvature -6- of the stomach. The surgeon thus has anatomical reference points and a guide for carrying out a closure resection (stapling) by resting against this Faucher tube 114 (steps 2&3). It should be noted that the combined operation of closure resection is carried out, in a manner known per se, by means of a surgical instrument designed for making an incision and for immediately closing the two edges of the wound by stapling.

It goes without saying that it would be much more convenient for the surgeons only to have to use a single catheter suitable for all the steps of the procedure. All the more so since the Salem catheters or Faucher tubes have not been specially designed for this longitudinal gastrectomy, and therefore have a number of drawbacks.

In particular, these utensils, usually made of silicone, lose their rigidity owing to the body heat. Thus, they do not maintain their position in the stomach and so make it difficult to perform the operation of closure resection by stapling.

Moreover, whether the longitudinal gastrectomy is carried out with or without conservation of the gastric antrum, the Salem catheters or the Faucher tubes do not provide any particular aid, in particular with respect to calibration of the portion of stomach to be preserved, which is still extremely difficult for the surgeon.

Another drawback with conventional catheters is that they risk being stapled during the operation. In fact, these catheters are difficult for the surgeon to see through the stomach wall, in coelioscopy. Therefore it may happen that the surgeon does not sufficiently accurately locate the positioning of the catheter before performing the section of the stomach using the resection-stapling tool and he staples this catheter with the stomach wall, sometimes going as far as complete section of the catheter. The consequences of such a mishap are potentially serious as there is then a very great risk of gastric leakage, with associated peritonitis, during ablation of the catheter that was accidentally stapled.

In addition, an orogastric catheter is known, which is used for the placement of gastric bands. This catheter, shown in FIG. 3, comprises a silicone tube 13, which is provided with graduated positioning marks 10, which is open at both ends and whose wall has oblong openings 115 in its distal part. The latter is also equipped with a balloon 11 enveloping the tube 13, i.e. said balloon 11 is traversed diametrically by the tube 13. This balloon 11 can be inflated via tube 12 arranged on the outside of tube 13 and connecting said balloon 11 to an inflating means 14 (blower closed by a valve thus permitting the injection of air) arranged in the proximal part of the calibration catheter. Once the distal part of the calibration catheter has been introduced into the oesophagus just above the stomach, the surgeon inflates the balloon 11 and uses the bulge thus created as a reference point for placing the gastric band in this junction zone between the abdominal part of the oesophagus and the stomach.

In these circumstances, it is clear that there is a real need for a novel orogastric catheter that is perfectly suitable for aiding the surgeon during longitudinal gastrectomy procedures.

The specification of this novel catheter would be that it makes it possible in itself:
1—to withdraw the air from the patient's stomach;
2—to calibrate the portion of stomach that remains, whatever the technique, with or without conservation of the gastric antrum, so that the exact volume of the stomach that remains is known. The choice of the type of cut is then made by the surgeon during the operation;
3—to enable the surgeon to take anatomical reference points and to guide him in performing the gastric section, easily, according to the technique that he has chosen, without the risk of cutting through the catheter;
4—to allow the injection or withdrawal of liquid for verifying the hermeticity of the suture.

Another specification of this novel orogastric catheter would be to have a tubular body of suitable shape and rigidity for correct, stable positioning in the stomach, taking into account the patient's body temperature, which makes the catheter more flexible, to facilitate the resection-stapling operation.

Another requirement of the surgeons for this novel orogastric catheter would be that it should be perfectly visible, to avoid it being stapled during the procedure.

Technical Problem—Objectives of the Invention

The technical problem that the present invention proposes to solve is to meet at least one of the objectives listed below:
to supply a novel orogastric catheter making it possible to improve the assistance offered to the surgeon during longitudinal gastrectomy procedures;
to supply a novel orogastric catheter for longitudinal gastrectomy that makes it possible in itself to carry out the four steps 1-4 mentioned above: exsufflation of the stomach, calibration of the portion of the stomach to be preserved, guidance and detection of anatomical reference points, then the injection and withdrawal of liquid, in particular for verifying the hermeticity of the suture line;
to supply a novel orogastric catheter for longitudinal gastrectomy that can be wedged perfectly in the stomach so as to facilitate the operation of closure resection by stapling by guiding the surgeon;
to supply a novel orogastric catheter for longitudinal gastrectomy that should be perfectly identifiable and visible by the surgeon, so as to avoid incidents such as stapling of the catheter;
to supply a novel orogastric catheter for longitudinal gastrectomy, which can easily be positioned in the stomach, which can thus be positioned durably without moving, without twisting, without being displaced and that can be withdrawn easily;
to supply a novel orogastric catheter that would make it possible to know the residual volume of the stomach that remains for performing good-quality resection;
to supply a novel multifunctional orogastric catheter that can be sterilized;
to supply a novel orogastric catheter for longitudinal gastrectomy that is economical and simple to manufacture and to use.

BRIEF DESCRIPTION OF THE INVENTION

Some or all of these objectives, among others, are achieved by the present invention, which relates to a novel orogastric catheter comprising a body whose distal part is in particular intended, in the context of the bariatric surgical technique of longitudinal gastrectomy, to guide the surgeon for resection of a part of the stomach and to define the closure line (stapling-suture) after resection.

This catheter is characterized in that this distal part carries a balloon having, in the inflated state, a shape substantially matching that of the pyloric antrum -4-, in such a way that it can be lodged in this pyloric antrum -4-, the end of the inflated balloon then preferably being in abutment against the pylorus -5- and the distal end of the body of the catheter for its part preferably being in abutment against the pyloric antrum -4-, while the part of the body of the catheter arranged above the inflated balloon is wedged against the wall of the lesser curvature -6- of the stomach -1-, and thus make it possible:
to determine the position of the start of the closure resection line in the area of the pyloric antrum -4-,
to define the closure resection line,
and to calibrate the pyloric antrum -4- and the gastric sleeve to be preserved.

This novel orogastric catheter makes it possible to perform longitudinal gastrectomy efficiently and reliably by reducing the capacity of the stomach by two thirds and thus give the patient a sensation of early satiety, leading to weight loss.

This novel orogastric catheter corrects the earlier difficulties of calibration of the portion of stomach to be removed. These difficulties could have the consequence that, without having sufficiently reduced the stomach, the latter dilates over time and the effect of the longitudinal gastrectomy is lost, so that the problem of the patient being overweight is unchanged.

This novel orogastric catheter therefore has a distal part which, once introduced into the stomach, can assume the shape of the pyloric antrum -4- by inflating the balloon. This distal appendage formed by the inflated balloon is intended to be in abutment against the pylorus -5- while resting on the pyloric antrum -4- and to allow wedging of this distal part of the catheter, and therefore its correct, stable positioning, for the purpose of closure resection preferably by stapling.

This novel multifunction orogastric catheter in particular improves this bariatric surgical technique by supplying valuable assistance to the surgeon. The procedure is carried out more easily, more rapidly, more reliably and more effectively with respect to the intended result.

According to an advantageous embodiment of the invention, the dimensions of the body of the catheter in right cross-section, i.e. the outside diameter De when the body is a round tube, determine the volume of stomach -1- preserved after resection, and the dimensions or the volume of the inflated balloon determine the volume of the pyloric antrum -4- preserved after resection.

To provide the best match to the anatomy of the lower part of the stomach, the inflated distal balloon preferably has a general (truncated) conical shape, preferably a truncated shape that is asymmetric and distorted with a terminal diameter Dt, a diameter at the base Db and a diameter Dm of the middle part, such that: $Dt < Db \leq Dm$; an end offset relative to the axis of the base of the balloon, upwards, towards the part of the body of the catheter arranged above the inflated balloon, in such a way that the upper face of the inflated balloon intended to be arranged opposite the angular notch -9- of the stomach -1-, has a less pronounced curvature than that of the lower face.

Moreover, to perfect the matching of shape with the anatomy of the pyloric antrum -4-, it is preferable, according to the invention, that the upper face of the inflated distal balloon, the face intended to be arranged opposite the angular notch -9- of the stomach -1-, should make, with the body of the catheter (preferably tubular of circular section), an angle α between 70 and 110°, preferably between 80 and 100° and even more preferably of the order of 90°.

To optimize the wedging of the distal part of the catheter in the stomach -1-, it is particularly advantageous according to the invention for the distal balloon to be mounted on the outer face of the wall of the catheter body (preferably tubular with right circular cross-section), in such a way that the distance d between the distal end of the body of the catheter and the point of the base of the inflated balloon closest to said distal end, is less than or equal to 30 mm, preferably less than or equal to 20 mm, and even more preferably is between 1 and 15 mm.

To improve the visibility of the catheter, it is envisaged, according to the invention, that the catheter body, preferably tubular of right circular cross-section, is provided with a reference mark enabling the surgeon to position the balloon correctly in the patient's stomach -1-, so that once inflated, this balloon can be lodged in abutment in the pyloric antrum -4-, said reference mark preferably comprising a mark coaxial to the body and arranged on some or all of the length, advantageously the entire length, of the wall of the body, on the same side as the balloon.

Advantageously, the body of the catheter is tubular and open at both ends, proximal and distal, the latter preferably being equipped with a tip of rounded shape to facilitate insertion in the patient's mouth and oesophagus.

In order to provide its function of transfer of liquid or gaseous fluids (steps 1 and 4 of the procedure) between the interior and exterior of the stomach, the preferably tubular body of the catheter defines a channel for circulation of fluid between the proximal opening and the distal opening, the latter preferably being formed by a plurality of lateral and/or terminal holes.

For inflating and deflating, the distal balloon provided with the catheter according to the invention preferably comprises a tube connecting the balloon to the proximal end of the body and allowing inflation/deflation of said balloon from this proximal end.

In a preferred embodiment, the catheter according to the invention comprises
- a tubular body of silicone with a length between 600 and 1200 mm, preferably between 700 and 1100 mm, and even more preferably between 850 and 950 mm and with an outside diameter De between 24 Fr and 75 Fr (i.e. between 8 mm and 25 mm), and preferably between 30 Fr and 40 Fr (i.e. between 10 mm and 13.33 mm), this body also being provided in its distal part with a rounded distal tip and with lateral holes intended to provide communication between the interior of the stomach and the exterior of the alimentary canal via the lumen of the tubular body;
- an inflated balloon 25 with a diameter at the base Db between 35 and 60 mm and with a height H of 50+/−10 mm, preferably +/−5 mm, and even more preferably +/−3 mm;
- a positioning reference mark formed by a contrasting mark over the entire length of the wall of the body, on the same side as the balloon 25, in the diametrical plane common to the body and to the balloon 25;
- and optionally means for deflecting the distal part of the catheter 20.

Ideally, the catheter is characterized in that H+De=50 to 100 mm, and even better 60 to 80 mm.

The optional means for deflecting the distal part of the catheter can be provided to make it possible to make an elbow on the distal part of the catheter, so as to follow the anatomy of the stomach -1-, once this distal part has been introduced into the latter. These deflecting means can, for example, comprise one or more control cables or cord(s) that can be operated by pulling, arranged along the tubular body of the catheter.

In other words, the catheter according to the invention is designed:
(i) to be introduced in the patient's mouth until its distal end reaches the patient's stomach,
(ii) to extract stomach fluids, in particular gaseous e.g. air in the case of air distension induced by the intubation manoeuvres during anaesthesia;
(iii) to inflate the balloon and lodge it in the pyloric antrum -4- in such a way that the end of the inflated balloon is in abutment against the pylorus -5-, that the distal end of the body of the catheter is in abutment against the pyloric antrum -4-, preferably at a distance of 5 to 10 cm, even better 6 to 8 cm from the pylorus -5-, and that the part of the body of the catheter arranged above the inflated balloon is wedged against the wall of the lesser curvature -6- of the stomach -1-,
(iv) on the one hand, to guide the surgeon for resection of a part of the stomach -1-, determining the position of the start of the line for resection and closure (stapling-suture) in the area of the pyloric antrum -4- and, on the other hand, to define the closure resection line, by giving him anatomical reference points and support for his instruments during these steps of closure resection,
(v) to calibrate the gastric sleeve and the pyloric antrum -4- to be preserved,
(vi) to inject and then withdraw coloured liquid in the patient's stomach -1-, after closure, to verify the hermeticity of the closure line (suture),
(vii) and optionally to introduce means for visualization (light source) into the stomach -1-.

The invention also relates to a surgical technique of longitudinal gastrectomy (or "sleeve gastrectomy") consisting of carrying out steps (i) to (vii) described above.

Means for visualization, such as an optical fibre, can be introduced at any time point of the procedure, and preferably once the latter has started, using a coaxial channel provided in the wall or in the lumen of the tubular body of the catheter.

DETAILED DESCRIPTION OF THE INVENTION

The invention described below is an example of implementation of the novel orogastric catheter according to the invention, referring to the appended drawings in which:

FIG. 5 is a detail side view of the distal part of the catheter on which the inflated balloon is mounted;

FIG. 6 is a front view of FIG. 5;

Figure 4:
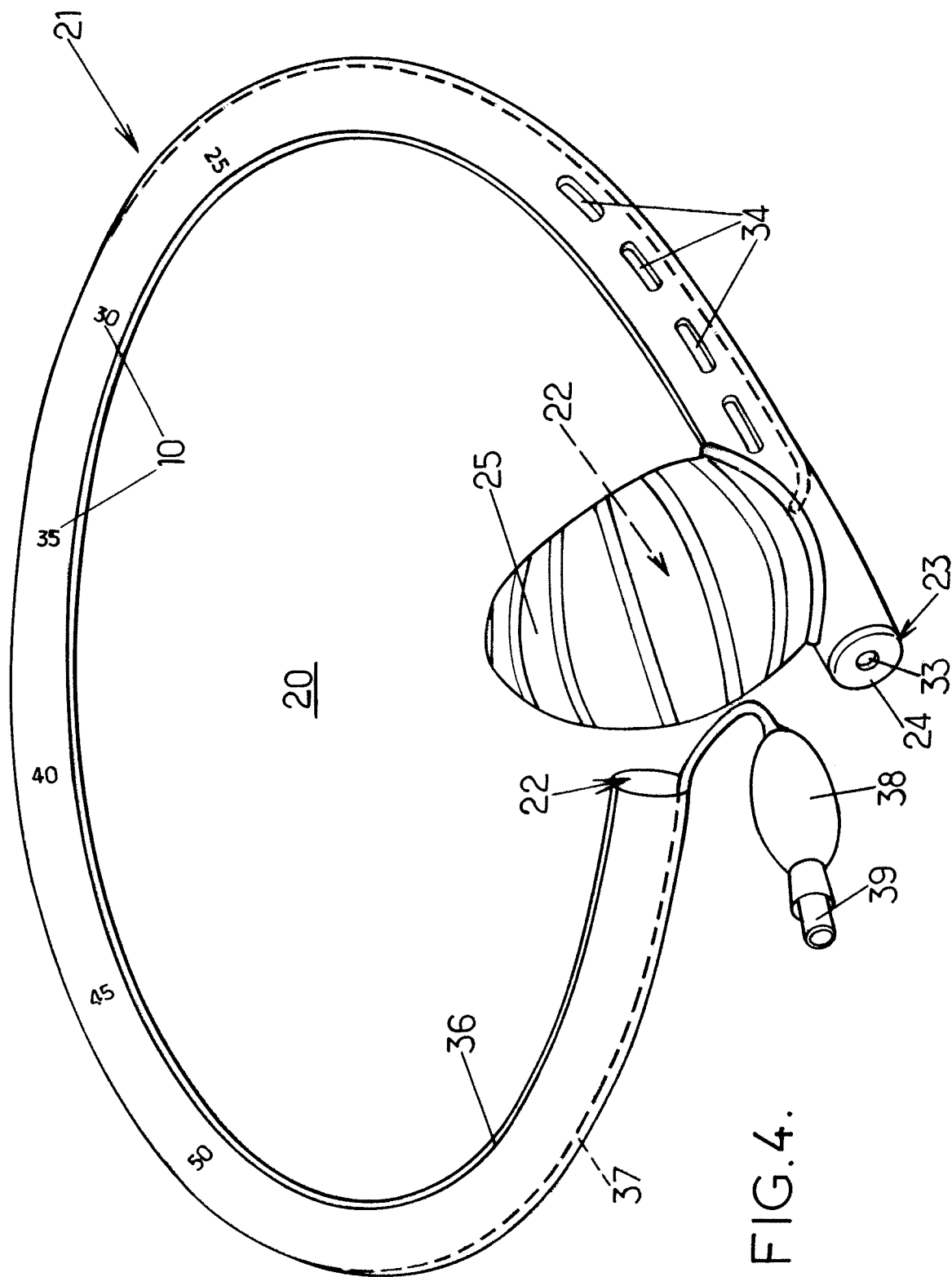
FIG. 4 is a general view of the novel orogastric catheter formed by a tubular body of circular section in silicone, the distal end of which is equipped with an inflated balloon, intended to become lodged in the pyloric antrum.

The orogastric catheter shown in its entirety in FIG. 4 and denoted by the general reference 20 comprises a tubular body 21 of silicone, of right circular cross-section. This tubular body 21 has an open proximal end 22 and a distal end 23, equipped with a distal tip 24. The outside diameter De shown in FIGS. 5 to 8 of this tubular body 21 is for example 12.5 mm, or 37.5 Fr (French bougies). This outside diameter De calibrates the volume of the stomach -1- to be preserved. Thus, several diameters of this tubular body 21 and therefore several calibres can be offered to the surgeon.

The total length of the tubular body 21 from the proximal end 22 to the distal end 23 is, for example, 900 mm.

Figure 1:
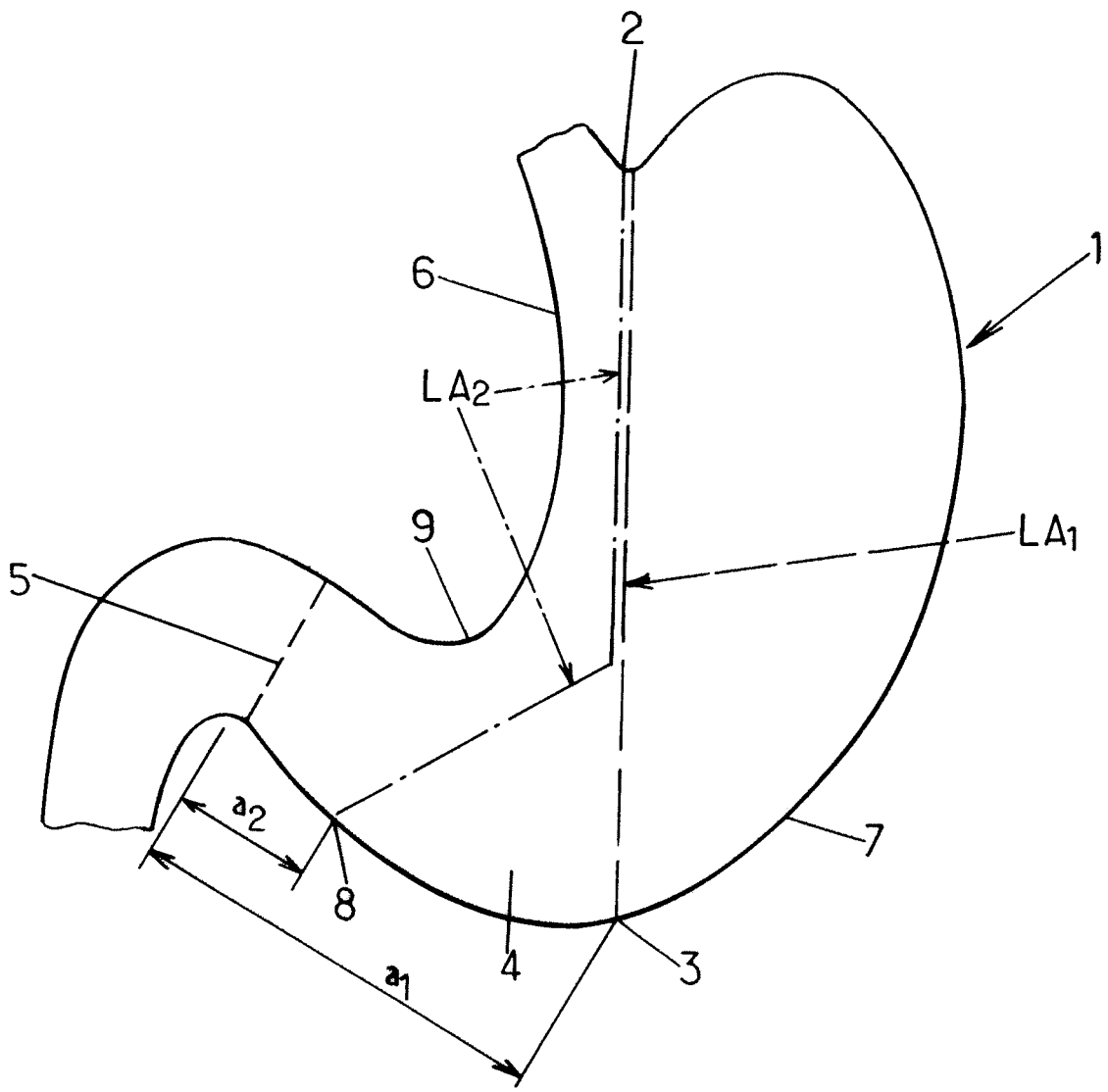
FIGS. 1 to 3 show, respectively, the anatomy of the stomach and two elements of the prior art.
Figure 2:
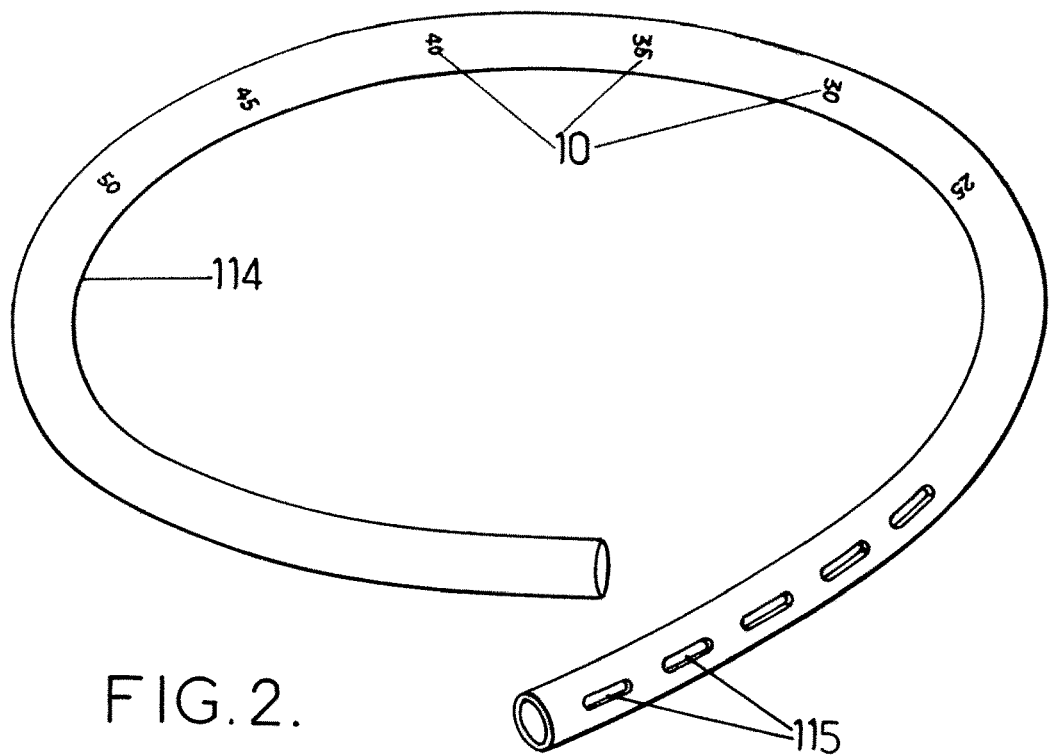
Figure 3:
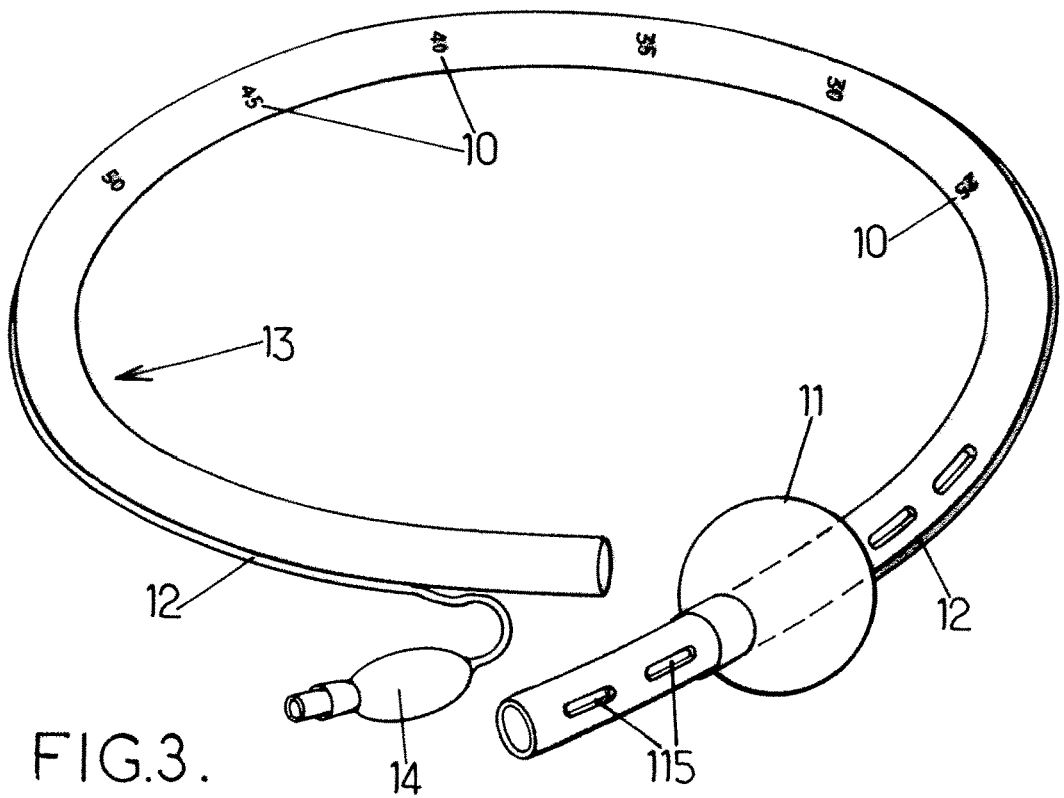
Figure 9:
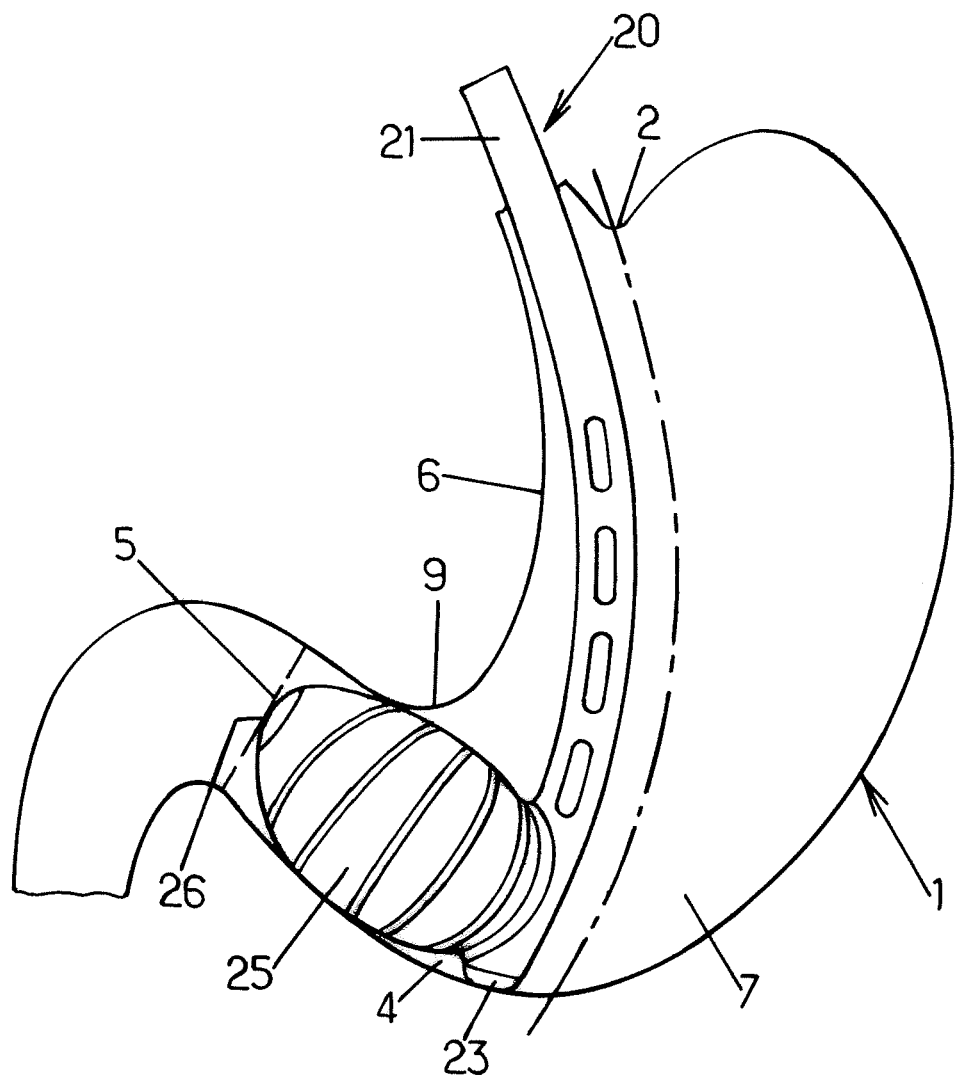
FIG. 9 is a schematic diagram showing the placement of the catheter in the stomach.

The tubular body 21 advantageously has a sufficient total length so that its distal part, in particular the inflated balloon 25, can be placed in the pyloric antrum -4- of the stomach -1- (cf. FIGS. 1 and 9). The tubular body 21 is preferably made of transparent silicone elastomer. Its structure, and its mechanical properties, in particular including its elasticity, are selected in such a way that the rigidity of the catheter is sufficient so that it can be introduced via the patient's mouth as far as the stomach, passing through the oesophagus, without damaging the walls of the alimentary canal, while preserving a substantially rectilinear shape to match the anatomical morphology of the patient's stomach -1-, in particular of the lesser curvature -6- of the stomach in the case of the tubular body 21 and the pyloric antrum -4- in the case of the inflated balloon 25. Thus, the tube e.g. of silicone elastomer forming the body of the catheter, the latter advantageously has a SHORE hardness of 65±10.

Advantageously, the tubular body 21 of the catheter 20 is graduated from 5 cm in 5 cm steps (10 graduations) starting from the distal end 23.

Moreover, the distal part of tube 21 of the catheter 20 carries a balloon 25 that has, in the inflated state, a shape substantially matching that of the pyloric antrum -4-. This balloon 25 is mounted on the outer face (right anatomical face—FIG. 9-) of the wall of the tubular body 21, in such a way that the median longitudinal plane of the inflated balloon 25 corresponds approximately to the median longitudinal plane of the tubular body 21.

These median longitudinal planes of the inflated balloon 25 and of the tube 21 are roughly equivalent to the frontal plane of anatomical section (FIG. 9).

This inflated balloon 25 has a general asymmetric and distorted truncated cone shape with, on the one hand, a terminal diameter Dt, a diameter at the base Db, and a diameter Dm of the middle part such that Dt<Db≤Dm, and, on the other hand, an end 26 that is offset, relative to the axis 27 of the base of the inflated balloon 25, upwards, towards the part of the tubular body 21 of the catheter 20 arranged above the inflated balloon 25, in such a way that the upper face of the inflated balloon 25 intended to be arranged opposite the angular notch -9- of the stomach -1-, has an upper curvature 29 {between points Cst and Csb in FIG. 5} of the upper face 28, less pronounced than the lower curvature 30 {between points Cit and Cib in FIG. 5} of the lower face. The radius of curvature of the upper curvature 29 (Cst-Csb) is greater than that of the lower curvature 30 (Cit-Cib).

The height H of the inflated balloon 25 is measured in the median longitudinal plane of the tubular body 21 and of the inflated balloon 25, from the edge of the tubular body 21 located just upstream of the distal tip 24 and downstream of the balloon 25 (right side of the stomach), to the top of the inflated balloon 25 (see FIG. 5).

For example: Db=40 mm; H=50 mm; Dm=50 mm and Dt=10 mm.

In other words, the dimensions and the elasticity of the balloon 25 are such that the volume of the inflated balloon can for example be 75 cm$^3$+/−25 cm$^3$. According to another feature of the invention, the upper face 28 of the inflated balloon 25 intended to be arranged opposite the angular notch -9- (cf. FIGS. 1 and 9) of the stomach -1- makes, with the tubular body 21 of the catheter 20, an angle $\alpha$ equal, in this example, to about 90° (cf. FIG. 5).

As is clear from FIG. 5, the angle $\alpha$ is defined by the straight line passing through the two points Csb and Cst of the inflated balloon (25) and by the tubular body 21-generator G.

This balloon 25 consists of a membrane, for example of silicone elastomer preferably made from several superposed annular segments 31, integral with one another, and with dimensions selected to give the inflated balloon 25 the shape described above and shown in FIGS. 4, 5, 6 and 9.

Figure 7:
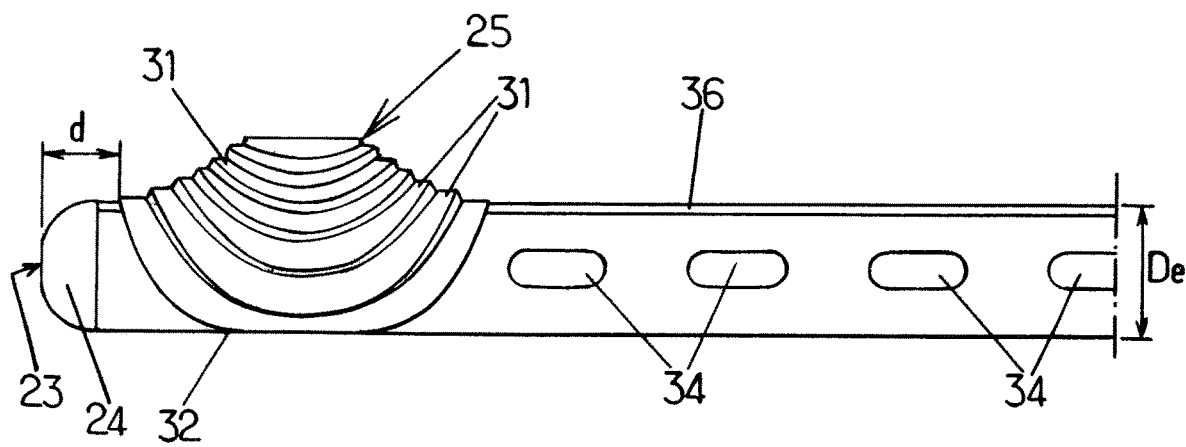
FIG. 7 is a side view of the distal part of the catheter with the balloon in the deflated state.
Figure 8:
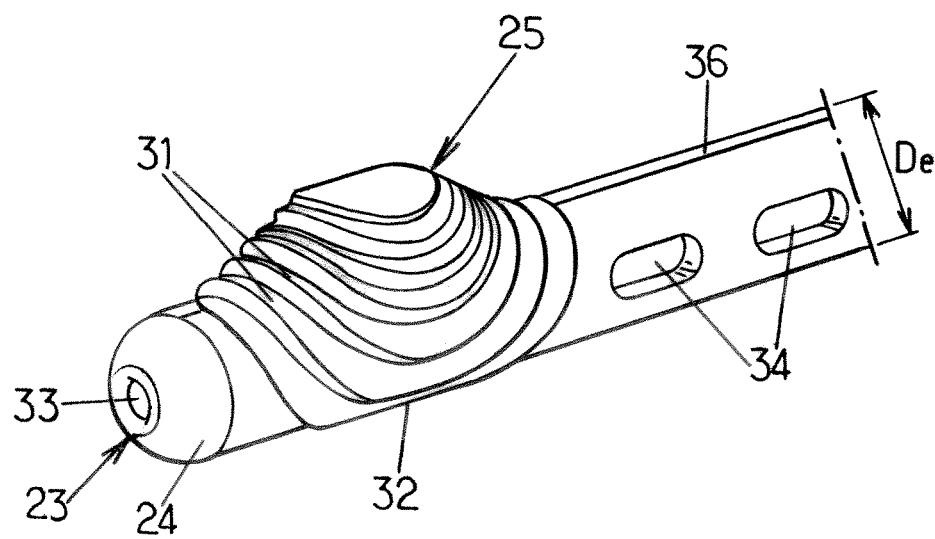
FIG. 8 is an enlargement of FIG. 7 according to a perspective view from ¾ front.

The base of balloon 25 has a lip 32 welded and/or glued on tube 21 of the catheter 20. As can be seen in FIGS. 7 and 8, the base 32 of balloon 25 envelops tube 21 on a large part of its circumference.

Moreover, as shown in FIG. 7, the distance d between, on the one hand, the distal end of tube 21 corresponding to the distal end 23 of tip 24 and, on the other hand, the point of the base of the inflated balloon 25 closest to this distal end 23, is, for example in the present case, 10 mm. It is advantageous that d should be as small as possible, so as to adapt best to the anatomical shape of the pyloric antrum -4-.

This rounded distal tip 24 is pierced in its centre with a hole 33 so that the lumen of tube 21 communicates with the exterior, in the same manner as the oblong lateral holes 34 present in the distal part of the tube 21, upstream of the balloon 25. These orifices 33, 34 permit the withdrawal and injection of gaseous or liquid fluids of the stomach.

According to the invention, calibration of the part of the stomach to be preserved is not only provided by the outside diameter De of the tubular body 21, but also by the volume of the inflated balloon 25. Several volumes of inflation of the balloon 25 give as many calibres to the surgeon.

The catheter 20 is also provided with a positioning reference mark 36. This reference mark 36 is formed by a contrasting mark on the entire length of the wall of tube 21 from the proximal end 22 to the distal end 23. It is perpendicular to the axis 27 of the inflated balloon 25, in the median longitudinal plane common to said inflated balloon 25 and to the tube 21. It is placed on the right side of the stomach, i.e. the side where the balloon 25 can be inflated in the pyloric antrum -4-. In particular it indicates to the surgeon the outer face of the wall of tube 21 on which the balloon 25 is mounted (anatomical right side in FIG. 9). This face is then in abutment against the lesser curvature. Placement of the inflated balloon 25 in the pyloric antrum -4- is thus greatly facilitated by this contrasting reference mark 36.

The catheter 20 according to the invention is also equipped with a tube 37 connecting the balloon 25 to the proximal end 22 of the tubular body 21 and allowing inflation/deflation of said balloon 25 from this proximal end, by means of an inflating means, which can be for example a bulb 38 provided at the proximal end 37 connected to the exterior via a valve 39, and/or a fluid (e.g. air) injector such as a syringe, which can be introduced into the tip of tube 37 upstream of valve 39. The inflating tube 37 of the balloon 25 passes along within the thickness of the wall of the tubular body 21 on the same side as the positioning reference mark 36 or on the other side. The distal end of the inflating tube 37 opens inside the distal balloon 25.

FIG. 9 shows the stable position of the distal part of the tubular body 21 against the lesser curvature -6- and the wedging of the inflated bulb 25 in the pyloric antrum -4-.

The positioning of the inflated balloon 25 and of the distal part of the tubular body 21 shown in FIG. 9 provides the surgeon with anatomical reference points and a guide for carrying out resection-stapling of the left part of the stomach -1- to be removed (dot-and-dash line in FIG. 9), following the calibration also defined by the inflated balloon and the distal part of tube 21 in abutment against the lesser curvature -6-.

The optional deflecting means that can allow folding of the distal part of the catheter, for example 88 mm from the distal end, by an angle e.g. of about 90°, comprise a cable or pull-cord system inserted in a channel coaxial with tube 21 on the right side of the stomach, where the balloon 25 is located. The cable passes down through this canal and is fixed in the distal part of the catheter. Above the fixing point of the cable, and of the distal tip 24 of the catheter 20, a notch with an angle of about 45° is made in the body 21 of the catheter 20 so as to create a folding line. A membrane is glued on the notch to ensure hermeticity of the body of the catheter. Once the catheter is in place in the patient's stomach -1-, the cable can be tightened by the action of the surgeon's hand at the proximal part of the catheter, and this action leads to folding or deflection of the terminal distal part of the tubular body 21 which forms an angle, for example of 90°, with the upper part of said tubular body 21.

The lumen of the tubular body 21 can allow introduction of visualizing means such as a light source, for example a flexible optical fibre.

It is possible to envisage a surface treatment of the outer face of the tubular body 21 and of the balloon 25, so as to reduce the coefficient of friction and thus facilitate sliding of the catheter 20 against the internal tissues of the patient's alimentary canal.

As shown in FIG. 9, this orogastric catheter 20 can be introduced, prior to longitudinal gastrectomy, in the patient's mouth until its distal end 23 reaches the stomach -1-. The sequence of longitudinal gastrectomy then consists of exsufflation of the stomach in the case of air distension induced by the intubation manoeuvres during anaesthesia, then inflating the balloon 25 and lodging it in the pyloric antrum -4-, in such a way that:

the end 26 of the inflated balloon 25 is for example in abutment against the pylorus -5- (shown by dotted lines in FIG. 9), so that the distal end 23 of the tubular body 21 is for example in abutment against the pyloric antrum -4-, for example about 5 to 10 cm from the pylorus -5-, and so that the part of the tubular body 21 of the catheter 20 arranged above the inflated balloon 25 is wedged against the wall of the lesser curvature of the stomach 6.

The surgeon can then proceed, using a suitable tool, to resection-stapling of the left part of the stomach (dot-and-dash line in FIG. 9), guided by the inflated balloon 25 and the distal part of tube 21, which itself indicates the start of the closure resection line and said closure resection line itself, also supplying, in addition to these anatomical reference points, a support for his closure resection instrument. The inflated balloon 25 and the distal part of tube 21 also calibrate the gastric sleeve and the pyloric antrum 4 to be preserved.

After resection of the left part and stapling, it is possible to inject coloured liquid in the patient's stomach 1 for verifying the hermeticity of the closure line.

The light source for visualizing the interior of the stomach can be introduced in the tubular body 21 at any time during the procedure.

The surgeon is thus provided with a multifunction orogastric catheter that enables him to perform high-quality longitudinal gastrectomy rapidly and in complete safety for the patient.

The invention claimed is:

1. An orogastric catheter for facilitating a longitudinal gastrectomy comprising a body whose distal part is in particular intended, in bariatric surgical technique of longitudinal gastrectomy, to guide a surgeon for resection of a part of a stomach and to define a closure line after resection, wherein the body extends between a proximal end and a distal end, and presents an outer face and a distal part close to the distal end, characterized in that wherein said distal part carries a balloon having a deflated state and an inflated state, wherein the balloon extends transversally from the outer face of the body and exclusively at one side of the body at a minimum distance d from the distal end of the body, wherein in the inflated state, the balloon has a shape and size substantially matching that of a pyloric antrum of the stomach, the inflated balloon having a truncated conical shape that is asymmetric, the balloon having a base attached to the body, an end opposite the base and a middle part between said base and said end, the balloon being distorted with a terminal diameter Dt at the end of the balloon, a diameter Db at the base of the balloon and a diameter Dm of the middle part of the balloon, with Dt<Db≤Dm; the end being offset relative to an axis of the base of the balloon, upwards towards a part of the body of the catheter arranged above the inflated balloon, so that an upper face of the inflated balloon directed towards the proximal end of the body and intended to be arranged opposite an angular notch of the stomach, has a less pronounced curvature than that of a lower face of the inflated balloon directed towards the distal end of the body, in such a way that the balloon can be lodged in said pyloric antrum, the end of the inflated balloon then being in abutment against the pylorus and the distal end of the body of the catheter being in abutment against the pyloric antrum, whereas a part of the body of the catheter arranged above the inflated balloon is wedged against a wall of the lesser curvature of the stomach, and to thus permit:

determining position for starting the resection closure line about the pyloric antrum, defining the resection closure line, and calibrating the pyloric antrum and a gastric sleeve to be preserved.

2. Catheter according to claim 1, wherein the inflated balloon has dimensions in cross-section determining a volume of the pyloric antrum preserved after resection and wherein the body has dimensions in cross-section determining a volume of stomach preserved after resection.

3. Catheter according to claim 1, wherein the inflated balloon is conformed so that an upper face of the inflated balloon intended to be arranged opposite the angular notch of the stomach makes, with the bod of the catheter an angle α between 70 and 110°.

4. Catheter according to claim 1, wherein the distance d between the distal end of the body of the catheter and a point of the base of the inflated balloon closest to said distal end, is less than or equal to 30 mm.

5. Catheter according to claim 1, wherein the body is provided with a reference mark enabling the surgeon to position the balloon correctly in the patient's stomach, so that once inflated, this balloon can be lodged in abutment in the pyloric antrum, said reference mark comprising a mark coaxial to the body and arranged on some or all of a length, of wall of the body, on the same side as the balloon.

6. Catheter according to claim 1, comprising a tube connecting the balloon to the proximal end of the body and an inflating device for inflation/deflation of said balloon from this proximal end through the tube.

7. Catheter according to claim 1, comprising:
a tubular body of silicone with a length between 600 and 1200 mm and with an outside diameter De between 8 mm and 25 mm, said body also being provided in its distal part with a rounded distal tip and lateral holes intended to provide communication between an inner stomach and an exterior of an alimentary canal via a lumen of the tubular body;
an inflated balloon with a diameter at the base Db between 35 and 60 mm and with a height H of 50+/−10 mm;
a positioning reference mark formed by a contrasting mark on the entire length of wall of the body, on a same side as the balloon, in a diametrical plane common to the body and to the balloon.

8. Catheter according to claim 7, wherein the tubular body and the balloon are sized so that H+De=50 to 100 mm.

* * * * *